US00PP09942P

United States Patent [19]

Brouwer

[11] Patent Number: Plant 9,942

[45] Date of Patent: Jul. 1, 1997

[54] SPATHIPHYLLUM PLANT NAMED ILLUSION

[75] Inventor: Wim A. J. Brouwer, Nootdorp, Netherlands

[73] Assignee: Milestone Agriculture Inc., Apopka, Fla.

[21] Appl. No.: 627,460

[22] Filed: Apr. 4, 1996

[51] Int. Cl.[6] ..... A01H 5/00

[52] U.S. Cl. ..... Plt./88.1

[58] Field of Search ..... Plt./88.1

*Primary Examiner*—James R. Feyrer
*Attorney, Agent, or Firm*—C. A. Whealy

[57] ABSTRACT

A distinct cultivar of Spathiphyllum plant named Illusion, characterized by its numerous leaves and side shoots and full, dense appearance; large leaves that are held horizontal to the petiole; rapid growth rate; early flowering; and numerous, large, long-lasting, pure white flowers positioned just above the foliage on strong and erect peduncles.

1 Drawing Sheet

The present invention relates to a new and distinct cultivar of Spathiphyllum plant, botanically known as Spathiphyllum, and hereinafter referred to by the cultivar name Illusion.

The new cultivar was discovered by the inventor in Nootdorp, Holland, as a naturally occurring mutation in a large population of plants of the cultivar Auslese (not patented). The new cultivar was identified as a single plant within this population of plants of the cultivar Auslese that was consistently more vigorous, fuller and held its leaves more horizontal than plants of the cultivar Auslese.

Asexual propagation of the new cultivar at Nootdorp, The Netherlands, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Kwintsheul, The Netherlands, in 14-cm containers in a glass greenhouse with an average day temperature of 22C, and average night temperature of 20C, and a light level of 200 to 225 lux.

The following traits have been repeatedly observed and are determined to be the unique characteristics of Illusion. These characteristics in combination distinguish Illusion as a new and distinct cultivar:

1. Numerous leaves and side shoots give a full, dense appearance.
2. Large leaves that are held horizontal to the petiole.
3. Rapid growth rate.
4. Early flowering.
5. Numerous large flowers that are positioned just above the foliage on strong and erect peduncles.
6. Pure white cupped spathe that curves over the top of the spadix.
7. Long-lasting flowers.

The new Spathiphyllum can be compared to its parent cultivar, the cultivar Auslese and is different from the cultivar Auslese in the following characteristics:

1. Plants of the cultivar Illusion are more vigorous, have more side shoots, and consequently are denser and fuller in appearance than plants of the cultivar Auslese.
2. Plants of the cultivar Illusion have larger leaves and flowers than plants of the cultivar Auslese.
3. Mature leaves of plants of the cultivar Illusion are not as glossy as mature leaves of plants of the cultivar Auslese.
4. Leaves of plants of the cultivar Illusion are flat and horizontal to the stem whereas leaves of plants of the cultivar Auslese are drooping.

5. The spathe on plants of the cultivar Illusion is cupped whereas the spathe on plants of the cultivar Auslese is straight and not curved.
6. Plants of the cultivar Illusion have short flower peduncles which position flowers just above the foliage. Plants of the cultivar Auslese have long flower peduncles and flowers are positioned higher above the foliage.

The new Spathiphyllum is similar to the cultivar Mauna Loa. The new Spathiphyllum differs from the cultivar Mauna Loa in the following characteristics:

1. Plants of the cultivar Illusion have more rounded leaves than plants of the cultivar Mauna Loa.
2. Mature leaves of plants of the cultivar Illusion are not as shiny as mature leaves of plants of the cultivar Mauna Loa.
3. Plants of the cultivar Illusion have more side shoots and are denser in appearance than plants of the cultivar Mauna Loa.
4. Plants of the cultivar Illusion have more flowers and flower earlier than plants of the cultivar Mauna Loa.
5. The spathe on plants of the cultivar Illusion is cupped whereas the spathe on plants of the cultivar Mauna loa is straight and not curved.
6. The spadix on plants of the cultivar Illusion is longer than the spadix on plants of the cultivar Mauna Loa.
7. Plants of the cultivar Illusion have shorter flower peduncles which position flowers just above the foliage. Plants of the cultivar Mauna Loa have longer flower peduncles and flowers are positioned higher above the foliage.
8. The spathe color on plants of the cultivar Illusion is whiter than the spathe color on plants of the cultivar Mauna Loa.
9. Flowers on plants of the cultivar Illusion are longer lasting than flowers on plants of the cultivar Mauna Loa.

The accompanying colored photograph illustrates the overall appearance of the new cultivar, showing the colors as true as it is reasonably possible to obtain in colored reproductions of this type. The photograph comprises a top perspective view of a typical potted plant of Illusion.

In the following description, color references are made to The Royal Horticultural Society Colour Chart except where general terms of ordinary dictionary significance are used.

Botanical classification: Spathiphyllum cultivar Illusion.

Parentage: Naturally occurring mutation of the cultivar Auslese.

Propagation: Divisions or by tissue culture.

Plant description:

*Plant shape.*—Upright, inverted triangle, symmetrical.

*Growth habit.*—Erect when young, becoming outwardly arching as leaves develop. Numerous side shoots give plants a full, dense appearance. Appropriate for 14-cm containers.

*Plant height.*—60 to 70 cm from soil level to top of leaf plane.

*Plant vigor.*—Vigorous, rapid grower.

*Crop time.*—Twenty weeks are usually require from planting of a young plant to a finished 14-cm container.

*Rooting habit.*—Freely branching, numerous fleshy roots with finer lateral roots.

*Foliage description.*—Leaf shape: Young: Narrowly ovate. Mature: Ovate. Leaf length: 26 to 29 cm. Leaf width: 13 to 15 cm. Margin: Entire. Leaf surface: Flat, not drooping. Leaf tip: Acuminate. Leaf base: Obtuse. Leaf aspect: Mature leaves held perpendicular to petiole, 90° angle. Leaf texture: Leathery, smooth, glabrous. Leaf color: Young, top side: Greener than 137B, glossy. Young, under side: 137C. Mature, top side: 137A/137B, not as glossy as immature leaves. Mature, under side: 137C. Petiole length, primary shoot: 50 to 60 cm. Petiole diameter, primary shoot, just below geniculum: About 5 mm. Geniculum diameter, primary shoots: About 6 mm. Petiole wing, primary shoots: Apparent on lower 75% of mature leaf petiole, about 8 mm wide at the midpoint. Petiole color: Young: 137C. Mature: Winged area: 137B. Above winged area: 137C. Geniculum: 137C. Venation: Top side: 137B/137C, sunken. Under side: 137C, prominent.

Flower description:

*Flower arrangement.*—Cupped spathe with spadix held just above the foliage. Flowers arise from leaf axils.

*Flower longevity.*—Flowers are long-lasting, generally maintaining white color for 10 to 12 weeks on the plant depending on light and temperature levels.

*Spathe.*—Shape: Ovate. Size: Length: About 15 cm. Width: About 9 cm. Aspect: Curves over the spadix. Color: Before unrolling: 155D. Open flower: White (155D) and shiny, turning green after pollination.

*Spadix.*—Size: Length: About 6 cm. Diameter: About 12 mm. Color: 8D at maturity, turning dark green after pollination.

*Peduncle.*—Aspect: Strong and erect. Size: Length: 70 to 80 cm. Diameter: About 5 mm. Color: 137C.

Disease resistance: No resistance to disease has been noted.

Seed development: Seed development is rarely observed.

It is claimed:

1. A new and distinct cultivar of Spathiphyllum plant named Illusion, as illustrated and described.

* * * * *

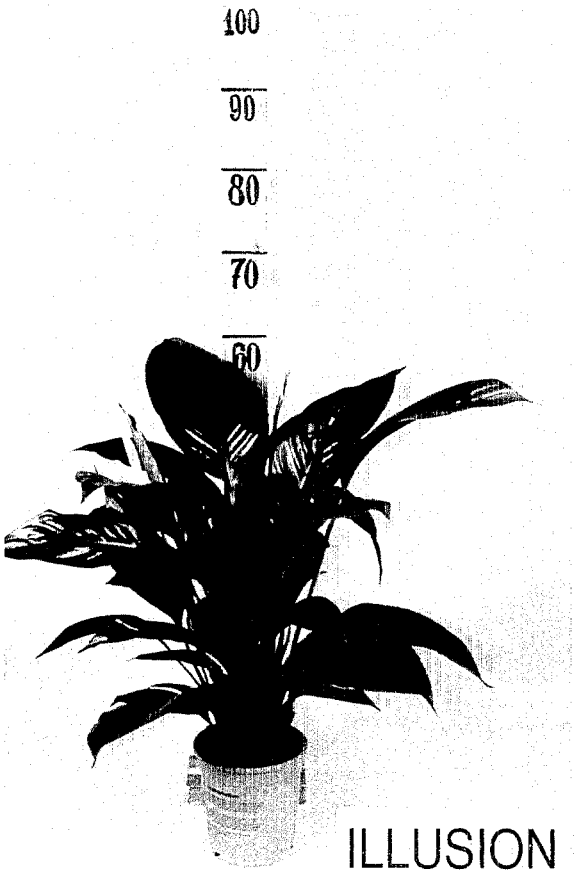
100
90
80
70
60
ILLUSION